United States Patent
Hartle

(10) Patent No.: US 8,769,869 B2
(45) Date of Patent: Jul. 8, 2014

(54) METHODS OF PREVENTING FLOODING IN MANUFACTURED SEED

(75) Inventor: Jeffrey E. Hartle, Bonney Lake, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 353 days.

(21) Appl. No.: 13/233,246

(22) Filed: Sep. 15, 2011

(65) Prior Publication Data

US 2012/0073194 A1 Mar. 29, 2012

Related U.S. Application Data

(60) Provisional application No. 61/387,244, filed on Sep. 28, 2010.

(51) Int. Cl.
*A01C 1/06* (2006.01)
*A01C 21/00* (2006.01)

(52) U.S. Cl.
USPC .......................................................... 47/57.6

(58) Field of Classification Search
USPC .............................. 47/57.6, 58.1 SE; 800/200
See application file for complete search history.

(56) References Cited

U.S. PATENT DOCUMENTS

| | | |
|---|---|---|
| 4,957,866 A | 9/1990 | Gupta et al. |
| 5,034,326 A | 7/1991 | Pullman et al. |
| 5,036,007 A | 7/1991 | Gupta et al. |
| 5,041,382 A | 8/1991 | Gupta et al. |
| 5,236,841 A | 8/1993 | Gupta et al. |
| 5,294,549 A | 3/1994 | Pullman et al. |
| 5,427,593 A * | 6/1995 | Carlson et al. ............ 47/57.6 |
| 5,482,857 A | 1/1996 | Gupta et al. |
| 5,563,061 A | 10/1996 | Gupta |
| 5,564,224 A | 10/1996 | Carlson et al. |
| 5,687,504 A | 11/1997 | Carlson et al. |
| 5,701,699 A | 12/1997 | Carlson et al. |
| 5,821,126 A | 10/1998 | Durzan et al. |
| 6,119,395 A | 9/2000 | Hartle et al. |
| 7,520,089 B2 | 4/2009 | Hartle et al. |
| 2003/0167684 A1 | 9/2003 | Carlson et al. |

OTHER PUBLICATIONS

Brown et al., "Osmotic requirement for Shoot Formation in Tobacco Callus," Physiol. Plant. 46:36-41 (1979).

Debergh et al., "Mass propagation of globe artichoke (*Cynara scolymus*): Evaluation of different hypotheses to overcome vitrification with special reference to water potential," Physiol. Plant. 53:181-187 (1981).

* cited by examiner

*Primary Examiner* — Kent L Bell
(74) *Attorney, Agent, or Firm* — Baker Hostetler LLP

(57) ABSTRACT

The invention provides methods of preventing flooding of a cavity within a shoot restraint of a manufactured seed by lowering the water potential of the nutritive media relative to the water potential of a plant embryo disposed within the cavity.

10 Claims, 1 Drawing Sheet

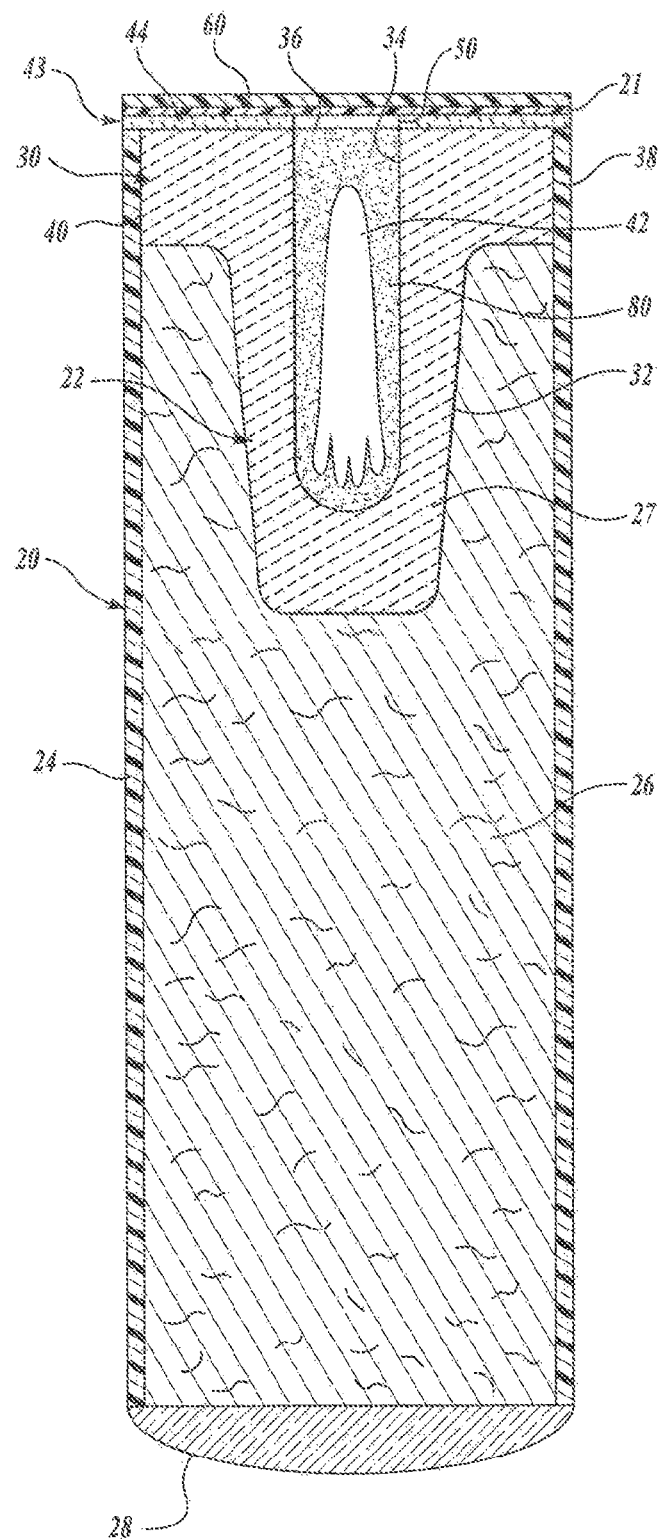

METHODS OF PREVENTING FLOODING IN MANUFACTURED SEED

CROSS-REFERENCE TO RELATED APPLICATION

This application is entitled to and claims the benefit of priority under 35 U.S.C. §119 from U.S. Provisional Patent Application Ser. No. 61/387,244 filed Sep. 28, 2010, and titled METHODS OF PREVENTING FLOODING IN MANUFACTURED SEED the contents of which are incorporated herein by reference.

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant. Plant embryos created by in vitro cultures, however, lack the natural protective and nutritive features of natural botanic seeds. Attempts have been made to provide the protective and nutritive structures found in natural botanic seeds to plant embryos cultured in a laboratory by using manufactured seeds. Manufactured seeds are described, for example, in U.S. Pat. Nos. 5,564,224; 5,687,504; 5,701,699; and 6,119,395.

Problems with manufactured seeds remain. Both the rate of successful germination and the quality of germinants produced from manufactured seeds are lower than the rate and quality obtained from natural botanic seeds. One of the problems encountered with manufactured seeds is that excess water may accumulate in the cavity of the manufactured seed that holds a plant embryo, and such condition may result in inhibition of germination, abnormal growth, and/or drowning of the embryo.

The flow of water into the cavity holding the embryo in a manufactured seed is a function of the relative water potentials of the components of the manufactured seed. Water potential is the potential energy of water per unit volume relative to pure water. Water potential is measured in Pascal units, with pure water having a potential of 0 Mpa. Water potential represents the flow of water from one area to another. Water will flow from an area of higher potential to an area of lower, or more negative, potential.

A manufactured seed, generally, comprises a seed coat, nutritive media, a shoot restraint, and a cavity within the shoot restraint that holds a plant embryo. In order for an embryo to survive and thrive in a manufactured seed, the embryo must be able to obtain water and nutrients from nutritive media. The relative water potential of the nutritive media, shoot restraint, and embryo must be such that the embryo has a more negative potential than the shoot restraint, which has a more negative potential than the nutritive media, so that the water and dissolved nutrients will flow from the nutritive media, through the shoot restraint, to the cavity, and to the embryo in the cavity. However, the relative differences in the water potentials of the components of a manufactured seed must be balanced so that the embryo receives a sufficient amount of water and nutrients without an excess amount of water flowing into the cavity so as to be detrimental to the embryo.

Therefore, there is a need to improve the rate of germination and the quality of germinants obtained from manufactured seeds by preventing an excess amount of water from flowing into the cavity of a manufactured seed, in which an embryo is disposed, while providing a sufficient amount of water and nutrients to the embryo. The present invention addresses these and other needs.

SUMMARY

In one aspect, the present invention provides a method of preventing flooding of a cavity within a shoot restraint of a manufactured seed comprising the steps of (a) assembling a manufactured seed comprising a seed coat and a shoot restraint, wherein the shoot restraint comprises a cavity; (b) lowering the water potential of nutritive media to be used in the manufactured seed, wherein the water potential of the nutritive media relative to the water potential of a plant embryo disposed in the cavity of the shoot restraint is such that an excessive amount of water does not flow out of the nutritive media and accumulate within the cavity, thereby preventing flooding of the cavity; and (c) adding the nutritive media prepared in step (b) to the manufactured seed.

In one embodiment, the water potential of the nutritive media is lowered by increasing the concentration of agar in the nutritive media. In one embodiment, the concentration of agar in the nutritive media is from about 26 g/L to about 30 g/L. In one embodiment, the concentration of agar in the nutritive media is from about 26 g/L to about 28 g/L. In one embodiment, the concentration of agar in the nutritive media is about 26 g/L.

In one embodiment the method of preventing flooding of a cavity within a shoot restraint of a manufactured seed further comprises the step of adding an adsorbent material to the cavity of the shoot restraint. In one embodiment the adsorbent material is charcoal. In one embodiment, the adsorbent material is nutrient-treated charcoal.

In one embodiment, the method of preventing flooding of a cavity within a shoot restraint of a manufactured seed further comprises the step of placing a plant embryo into the cavity of the shoot restraint.

It is to be understood that the order of the steps in the method may be altered without departing from the scope of the invention. For example, a plant embryo, an adsorbent material, and the nutritive media may be added to the manufactured seed in any order.

In one embodiment the method of preventing flooding of a cavity within a shoot restraint of a manufactured seed further comprises the step of culturing the manufactured seed under conditions suitable for germination of the plant embryo.

In one aspect the present invention provides a manufactured seed comprising a seed coat, a shoot restraint, wherein the shoot restraint comprises a cavity; and a nutritive media comprising agar at a concentration from about 26 g/L to about 30 g/L, whereby the concentration of agar in the nutritive media lowers the water potential of the nutritive media, wherein the water potential of the nutritive media relative to the water potential of an embryo disposed in the cavity of the shoot restraint is such that an excessive amount of water does not flow out of the nutritive media and accumulate within the cavity, thereby preventing flooding of the cavity. In one embodiment, the concentration of agar in the nutritive media is from about 26 g/L to about 28 g/L. In one embodiment, the concentration of agar in the nutritive media is about 26 g/L.

In one embodiment, the manufactured seed further comprises an adsorbent material within the cavity of the shoot restraint. In one embodiment, the adsorbent material within the cavity is charcoal. In one embodiment, the adsorbent material within the cavity is nutrient-treated charcoal. In one embodiment, the manufactured seed further comprises a plant embryo disposed in the cavity of the shoot restraint.

In one aspect the present invention provides a nutritive media comprising agar at a concentration from about 26 g/L to about 30 g/L for use in a manufactured seed, wherein the manufactured seed comprises a seed coat, a shoot restraint, and a cavity within the shoot restraint, whereby the concentration of agar in the nutritive media lowers the water potential of the nutritive media, wherein the water potential of the nutritive media relative to the water potential of an embryo disposed in the cavity of the shoot restraint is such that an excessive amount of water does not flow out of the nutritive media and accumulate within the cavity, thereby preventing flooding of the cavity.

In one embodiment the concentration of agar in the nutritive media is from about 26 g/L to about 28 g/L. In one embodiment the concentration of agar in the nutritive media is about 26 g/L.

DESCRIPTION OF THE DRAWINGS

The foregoing aspects and many of the attendant advantages of this invention will become more readily appreciated as the same become better understood by reference to the following detailed description, when taken in conjunction with the accompanying drawing, wherein the drawing is a side cross-sectional planar view of an exemplary manufactured seed comprising an embryo for use in the methods of the present invention.

DETAILED DESCRIPTION

Unless specifically defined herein, all terms used herein have the same meaning as they would to one skilled in the art of the present invention.

Unless stated otherwise, all concentration values that are expressed as percentages are weight per volume percentages.

As used herein, the term "flooding" refers to the condition in a manufactured seed that results when excessive amounts of water flow out of the nutritive media to the cavity in which a plant embryo is disposed and water accumulates in the cavity, thereby flooding the cavity.

As used herein, the term "water potential" refers to the tendency of water to move from one area to another. Typically, water potential is a negative value. Water moves from an area of higher water potential (less negative) to an area of lower water potential (more negative). The greater the difference in water potentials between two areas, the more water will flow from the area of higher water potential to the area of lower water potential.

A manufactured seed, generally, comprises a seed coat, nutritive media, a shoot restraint, and a cavity within the shoot restraint that holds a plant embryo. In order for a plant embryo to survive and thrive in a manufactured seed, the embryo must be able to obtain water and nutrients from nutritive media. The water potentials of the nutritive media, shoot restraint, and embryo, relative to each other, must be such that the embryo has a more negative water potential than the shoot restraint, which has a more negative water potential than the nutritive media, so that the water and dissolved nutrients will flow from the nutritive media, through the shoot restraint, to the cavity, and to the embryo in the cavity, while avoiding flooding of the cavity. Excess water in the cavity that holds an embryo may result in inhibition of germination, abnormal growth, and/or drowning of the embryo.

The problem of flooding of a cavity holding a plant embryo in a manufactured seed has been challenging to resolve. One reason the flooding problem has been difficult to resolve is the complex nature of water relations in a manufactured seed. The relative differences in the water potentials of the components of a manufactured seed must be balanced so that the embryo receives a sufficient amount of water and nutrients without an excess amount of water flowing into the cavity so as to be detrimental to the embryo.

Numerous efforts have been made by the inventor of the instant application to solve the flooding problem, including the use of different methods of sealing the manufactured seed; increasing the temperature at which the gelling agent in the nutritive media is processed during the manufacturing process; the use of different gelling agents; the use of different types of charcoal; and changing the storage environment. The aforementioned efforts to solve the flooding problem have had varying degrees of success.

The inventor of the instant application has found that by lowering the water potential of the nutritive media used in a manufactured seed relative to the water potential of a plant embryo disposed within the manufactured seed, an excessive amount of water does not flow out of the nutritive media and accumulate within the cavity of the manufactured seed holding a plant embryo, thereby preventing flooding of the cavity.

One method of lowering the water potential of the nutritive media used in a manufactured seed is to increase the concentration of agar. Typically, the concentration of agar in the nutritive media in a manufactured seed is about 18 g/L. The inventor of the instant application, after much effort, has discovered that an increased concentration of agar in the nutritive media from about 26 g/L to about 30 g/L is effective in preventing an excess amount of water from flowing out of the nutritive media to the cavity within the shoot restraint, thereby preventing flooding of the cavity. Furthermore, the inventor has found that a nutritive media having a concentration of agar from about 26 g/L to about 30 g/L releases enough water and dissolved nutrients to maintain a healthy embryo disposed in the manufactured seed. This result was surprising because embryos germinated on agar plates in which the concentration of agar in the media is 26 g/L germinate at a much slower rate than embryos germinated on agar plates in which the concentration of agar in the media is the standard concentration of 8 g/L. In contrast to agar plates, slower germination rates were not seen in manufactured seeds in which the concentration of agar in the nutritive media is 26 g/L. Moreover, advantages of the claimed method include that an increased agar concentration is easily integrated into the manufacturing process, and manufactured seeds having a nutritive media with increased agar concentration do not require any special handling or storage conditions.

In one aspect, the present invention provides a method of preventing flooding of a cavity within a shoot restraint of a manufactured seed comprising the steps of: (a) assembling a manufactured seed comprising a seed coat and a shoot restraint, wherein the shoot restraint comprises a cavity; (b) lowering the water potential of nutritive media to be used in the manufactured seed, wherein the water potential of the nutritive media relative to the water potential of a plant embryo disposed in the cavity of the shoot restraint is such that an excessive amount of water does not flow out of the nutritive media and accumulate within the cavity, thereby preventing flooding of the cavity; and (c) adding the nutritive media prepared in step (b) to the manufactured seed.

In one embodiment, the water potential of the nutritive media is lowered by increasing the concentration of agar in the nutritive media. In one embodiment, the concentration of agar in the nutritive media is from about 26 g/L to about 30 g/L. In one embodiment, the concentration of agar in the nutritive media is from about 26 g/L to about 28 g/L. In one embodiment, the concentration of agar in the nutritive media is about 26 g/L.

In one embodiment the method of preventing flooding of a cavity within a shoot restraint of a manufactured seed further comprises the step of adding an adsorbent material to the cavity of the shoot restraint. In one embodiment the adsorbent material is charcoal. In one embodiment, the adsorbent material is nutrient-treated charcoal.

In one embodiment, the method of preventing flooding of a cavity within a shoot restraint of a manufactured seed further comprises the step of placing a plant embryo into the cavity of the shoot restraint.

It is to be understood that the order of the steps in the method may be altered without departing from the scope of the invention. For example, a plant embryo, an adsorbent material, and the nutritive media may be added to the manufactured seed in any order.

In one embodiment the method of preventing flooding of a cavity within a shoot restraint of a manufactured seed further comprises the step of culturing the manufactured seed under conditions suitable for germination of the plant embryo.

Conditions suitable for germination of manufactured seeds are standard in the art and include conditions suitable for germination of natural seeds. For example, the manufactured seeds may be sown in any of a variety of environments, such as in sand, vermiculite, sterile soil, and/or in the field (natural soil). For example, sterile Coles™ washed sand, which is available from a variety of gardening supply stores, may be used.

In one aspect the present invention provides a manufactured seed comprising a seed coat, a shoot restraint, wherein the shoot restraint comprises a cavity; and a nutritive media comprising agar at a concentration from about 26 g/L to about 30 g/L, whereby the concentration of agar in the nutritive media lowers the water potential of the nutritive media, wherein the water potential of the nutritive media relative to the water potential of an embryo disposed in the cavity of the shoot restraint is such that an excessive amount of water does not flow out of the nutritive media and accumulate within the cavity, thereby preventing flooding of the cavity. In one embodiment the concentration of agar in the nutritive media is from about 26 g/L to about 28 g/L. In one embodiment the concentration of agar in the nutritive media is about 26 g/L.

In one embodiment, the manufactured seed further comprises an adsorbent material within the cavity of the shoot restraint. In one embodiment, the adsorbent material within the cavity is charcoal. In one embodiment, the adsorbent material within the cavity is nutrient-treated charcoal. In one embodiment, the manufactured seed further comprises a plant embryo disposed in the cavity of the shoot restraint.

The accompanying drawing is a side cross-sectional planar view of an exemplary manufactured seed 20 for use in the methods of the invention comprising a plant embryo 42 disposed within. In the exemplary embodiment shown in the drawing, the manufactured seed 20 comprises a seed coat 24, nutritive media 26, a dead end seal 28, and a shoot restraint 22. As shown in the drawing, the embryo 42 is disposed within a cavity 34 within the shoot restraint 22, is in functional contact with nutritive media 26, and is suitably sealed therein by a live end seal 43. It will be understood that the drawing provides a representative embodiment of a manufactured seed 20; however, the method of the invention is not limited to the particular embodiment of the manufactured seed shown in the drawing.

As used herein, a "seed coat" refers to a structure analogous to a natural seed coat that protects the plant embryo and other internal structures of the manufactured seed from mechanical damage, desiccation, from attack by microbes, fungi, insects, nematodes, birds, and other pathogens, herbivores, and pests, among other functions. The seed coat 24 may be fabricated from a variety of materials including, but not limited to, cellulosic materials, glass, plastic, moldable plastic, cured polymeric resins, paraffin, waxes, varnishes, and combinations thereof such as a wax-impregnated paper. The materials from which the seed coat is made are generally non-toxic and provide a degree of rigidity. The seed coat can be biodegradable, although typically the seed coat remains intact and resistant to penetration by plant pathogens until after emergence of the germinating embryo. The seed coat may be formed from a section of tubular material. The seed coat may be a sectioned straw of fibrous material, such as paper. The sections of straw may be pretreated in a suitable coating material, such as wax. Alternatively, the seed coat may be formed from a tubular section of biodegradable, plastic material. One such material is polylactic acid ("PLA") and is sold by NAT-UR of Los Angeles, Calif. Another suitable material is a polycaprolactone ("PCL") mixture, such as CAPA 6800 (Perstorp Polyols Inc., Toledo, Okla. 43612) with or without a 1% Tegomer H SI6440 plasticizer (Degussa Goldschmidt Chemical Corp, 914 East Randolph Road, Hopewell, Va. 23860). Such biodegradable plastic tubes may or may not require a wax coating as such tubes are already resistive to environmental elements. Additives such as antibiotics and plant-growth regulators may be added to the seed coat, for example, by incorporation into the material forming one or more of the layers of the seed coat or by coating or otherwise treating the layer(s) with the additive by conventional means.

In accordance with the manufactured seeds and methods of the invention, nutritive media 26 is in functional contact with the plant embryo disposed within the manufactured seed 20. As used herein, a "nutritive media" refers to a source of nutrients, such as vitamins, minerals, carbon, and energy sources, and other beneficial compounds used by the embryo during germination. Thus, the nutritive media 26 is analogous to the gametophyte of a natural seed. A nutritive media 26 according to the invention may include a substance that causes the media to be a semi-solid or have a congealed consistency under normal environmental condition. Typically, the nutritive media 26 is in the form of a hydrated gel. A "gel" is a substance that is prepared as a colloidal solution and that will, or can be caused to, form a semi-solid material. Such conversion of a liquid gel solution into a semi-solid material is termed herein "curing" or "setting" of the gel. A "hydrated gel" refers to a water-containing gel. Such gels are prepared by first dissolving in water (where water serves as the solvent or "continuous phase") a hydrophilic polymeric substance (serving as the solute or "disperse phase") that, upon curing, combines with the continuous phase to form the semi-solid material. Thus, the water becomes homogeneously associated with the solute molecules without experiencing any substantial separation of the continuous phase from the disperse phase. However, water molecules can be freely withdrawn from a cured hydrated gel, such as by evaporation or imbibition by a germinating embryo. When cured, these gels have the characteristic of compliant solids, like a mass of gelatin, where the compliance becomes progressively less and the gel becomes more "solid" to the touch as the relative amount of water in the gel is decreased.

In addition to being water-soluble, suitable gel solutes are neither cytotoxic nor substantially phytotoxic. As used herein, a "substantially non-phytotoxic" substance is a substance that does not interfere substantially with normal plant development, such as by killing a substantial number of plant cells, substantially altering cellular differentiation or maturation, causing mutations, disrupting a substantial number of cell membranes or substantially disrupting cellular metabolism, or substantially disrupting other process.

In the nutritive media and manufactured seed of the invention, the hydrated gel substance is agar. In one aspect the present invention provides a nutritive media comprising agar at a concentration from about 26 g/L to about 30 g/L, whereby the concentration of agar in the nutritive media lowers the water potential of the nutritive media, wherein the water potential of the nutritive media relative to the water potential of an embryo disposed in the cavity of the shoot restraint of a manufactured seed is such that an excessive amount of water does not flow out of the nutritive media and accumulate within the cavity, thereby preventing flooding of the cavity.

In one embodiment, the concentration of agar in the nutritive medium is from about 26 g/L to about 28 g/L. In one embodiment, the concentration of agar in the nutritive medium is about 26 g/L.

The nutritive media 26 typically comprises one or more carbon sources, an adsorbent material, vitamins, and minerals. Suitable carbon sources include, but are not limited to, monosaccharides, disaccharides, and/or starches. Suitable adsorbent materials include, but are not limited to charcoal, polyvinyl polypyrolidone, and silica gels. Charcoal used as an adsorbent material may be nutrient-treated. As used herein, "nutrient-treated" charcoal refers to charcoal that has been treated with a media that contains a variety of nutrients, such as a carbon source, vitamins, minerals, and amino acids, so that the charcoal absorbs and retains nutrients from the media. A representative media used to prepare nutrient-treated charcoal is media KE64-50. A representative method for preparing nutrient-treated charcoal is described in Example 2.

The nutritive media 26 may also comprise amino acids and a smoke suspension. Suitable amino acids may include amino acids commonly found incorporated into proteins as well as amino acids not commonly found incorporated into proteins, such as argininosuccinate, citrulline, canavanine, ornithine, and D-stereoisomers. A suitable smoke suspension contains one or more compounds generated through the process of burning organic matter, such as wood or other cellulosic material. Solutions containing these by-products of burning organic matter may be generated by burning organic matter, washing the charred material with water, and collecting the water. Solutions may also be obtained by heating the organic matter and condensing and diluting volatile substances released from such heating. Certain types of smoke suspensions may be purchased from commercial suppliers, for example, Wright's Concentrated Hickory Seasoning Liquid Smoke (B&G Foods, Inc. Roseland, N.J. 07068). Smoke suspension may be incorporated into the nutritive media 26 in any of various forms. For instance, smoke suspension may be incorporated as an aerosol, a powder, or as activated clay. An exemplary concentration of Wright's Concentrated Hickory Seasoning Liquid Smoke liquid smoke suspension, if present, is between 0.0001 ml and 1 ml of smoke suspension per liter of media. The nutritive media 26 may also include one or more compounds involved in nitrogen metabolism, such as urea or polyamines.

The nutritive media 26 may include oxygen-carrying substances to enhance both the absorption of oxygen and the retention of oxygen by the nutritive media 26, thereby allowing the media to maintain a concentration of oxygen that is higher than would otherwise be present in the media solely from the absorption of oxygen from the atmosphere. Exemplary oxygen-carrying substances include perfluorocarbons such as FC-77 (3M Corporation, St. Paul, Minn.), emulsified with a surfactant such as Pluronic F-68, available from BASF Corp., Parsippany, N.J. Exemplary oxygen-carrying substances are described in U.S. Pat. No. 5,564,224 (e.g., Col. 9, line 44, to Col. 11, line 67), herein incorporated by reference.

The nutritive media 26 may also contain hormones. Suitable hormones include, but are not limited to, abscisic acid, cytokinins, auxins, and gibberellins. Abscisic acid is a sesquiterpenoid plant hormone that is implicated in a variety of plant physiological processes (see, e.g., Milborrow, *J. Exp. Botany* 52:1145-1164 (2001); Leung & Giraudat *Ann. Rev. Plant Physiol. Plant Mol. Biol.* 49:199-123 (1998)). Auxins are plant growth hormones that promote cell division and growth. Exemplary auxins for use in the germination media include, but are not limited to, 2,4-dichlorophenoxyacetic acid, indole-3-acetic acid, indole-3-butyric acid, naphthalene acetic acid, and chlorogenic acid. Cytokinins are plant growth hormones that affect the organization of dividing cells. Exemplary cytokinins for use in the germination media include, but are not limited to, e.g., 6-benzylaminopurine, 6-furfurylaminopurine, dihydrozeatin, zeatin, kinetin, and zeatin riboside. Gibberellins are a class of diterpenoid plant hormones (see, e.g., Krishnamoorthy *Gibberellins and Plant Growth*, John Wiley & Sons, (1975)). Representative examples of gibberellins useful in the practice of the present invention include gibberellic acid, gibberellin 3, gibberellin 4, and gibberellin 7. An example of a useful mixture of gibberellins is a mixture of gibberellin 4 and gibberellin 7 (referred to as gibberellin 4/7), such as the gibberellin 4/7 sold by Abbott Laboratories, Chicago, Ill.

The nutritive media 26 may also include antimicrobials. Suitable antimicrobials are available from Sigma-Aldrich, St. Louis, Mo., sold as Product #A5955. Antimicrobials may be used, for example, at a concentration of 1 ml/L.

When abscisic acid is present in the nutritive media 26, it is typically used at a concentration in the range of from about 1 mg/L to about 200 mg/L. When present in the nutritive media 26, the concentration of gibberellin(s) is typically between about 0.1 mg/L and about 500 mg/L. Auxins may be used, for example, at a concentration of from 0.1 mg/L to 200 mg/L. Cytokinins may be used, for example, at a concentration of from 0.1 mg/L to 100 mg/L.

Exemplary nutritive media are described in U.S. Pat. No. 5,687,504 (e.g., Col. 8, line 63, to Col. 9, line 41) and in U.S. Patent Publication No. 2003/0167684, herein incorporated by reference. A representative nutritive media 26 is KE64-50, the composition of which is set forth in Table 1 below. A representative method for preparing a nutritive media useful in the present invention is described in Example 1.

The shoot restraint 22 of a manufactured seed is suitably manufactured from a porous material having a hardness strong enough to resist puncture or fracture by a germinating embryo, such as a ceramic or porcelain material, and includes an end seal portion 30 and a cotyledon restraint portion 32. The restraint portion 32 has an interior surface for contacting and surrounding at least the shoot end of a plant embryo and resists penetration by the shoot end during germination. The shoot restraint prevents the shoot end of the embryo, such as the cotyledons, from growing into and becoming entrapped in the nutritive media (also referred to as nutritive media). The cotyledon restraint portion 32 is suitably integrally or unitarily formed with the end seal portion 30. The shoot restraint 22 also includes a longitudinally extending cavity 34 extending through the end seal portion 30 and partially through one end of cotyledon restraint portion 32. The open end of the cavity 34 is known as a cotyledon restraint opening 36. The cavity 34 is sized to receive a plant embryo 42 therein. As shown in the drawing, the shoot restraint 22 comprises a plurality of pores 27, wherein the pores 27 allow the nutritive media 26 access into the inside of the cavity 34 comprising the embryo 42 and, therefore, allows the nutritive media 26 to functionally contact the embryo 42 under conditions sufficient to generate a conditioned embryo, as described herein.

The restraint is porous to allow access of the embryo to water, nutrients, and oxygen. The shoot restraint may be fabricated from any suitable material, including, but not limited to, glassy, metal, elastomeric, ceramic, clay, plaster, cement, starchy, putty-like, synthetic polymeric, natural polymeric, and adhesive materials. Exemplary shoot restraints are described in U.S. Pat. No. 5,687,504 (e.g., Col. 3, line 61, to Col. 4, line 13; Col. 18, line 7, to Col. 22, line 2), herein incorporated by reference.

All or only part of the plant embryo 42 may be inserted into the shoot restraint 22. Typically, at least the shoot end of the embryo is inserted into the shoot restraint 22. The surface area of nutrient uptake in a manufactured seed 20 is limited to the area of the plant embryo 42 that is in direct contact with the interior surface of the shoot restraint 22. During germination of plant embryos, the cotyledons have been found to be the primary organs for nutrient uptake (Brown & Gifford, *Plant Physiol.* 33:57-64 (1958)).

Either the interior surface of the shoot restraint 22 or the plant embryo 42, or both, may be contacted with a hydrated gel either before or after inserting the plant embryo 42 into the shoot restraint 22. Exemplary embodiments of hydrated gels are as described above for the nutritive media 26. The hydrated gel may comprise only gel solutes and water, or it may comprise plant nutrients and other substances, as described for the nutritive media 26.

The interior surface of the shoot restraint may be contacted with a hydrated gel solution that will cure to form a hydrated gel. A cavity 34 may then be made into the hydrated gel in the shoot restraint 22 and the plant embryo 42 inserted into the cavity 34 in the hydrated gel in the shoot restraint 22. In addition, or alternatively, at least a portion of the plant embryo 42 (such as the cotyledons) may be contacted with a hydrated gel solution that will cure to form a hydrated gel before inserting the plant embryo 42 into the shoot restraint 22.

As further shown in the drawing, adsorbent material 80 either completely or partially surrounds the embryo 42 in the cavity 34 and increases the surface area of the embryo 42 in functional contact with the nutritive media 26, thereby providing multiple pathways for the nutrients from the nutritive media 26 to pass to the embryo 42. Suitable adsorbent materials include activated charcoal, Dowex resins, zeolites, alumina, clay, diatomaceous earth, silica gel, and Kieselguhr. During assembly of the manufactured seed 20, the adsorbent material 80 is deposited into the cavity 34 in any manner known in the art, including manually. The adsorbent material 80 is preferably, but not necessarily, deposited within the cavity 34 such that it substantially centers the plant embryo 42 within the cavity 34. Although it is preferred that the adsorbent material 80 substantially centers the plant embryo 42 within the cavity 34, the plant embryo 42 need not be so positioned. The adsorbent material 80 need only position the plant embryo 42 within the cavity 34 in any manner to place the plant embryo 42 into functional contact with the nutritive media 26. Further, it is not necessary for the adsorbent material 80 to "surround" the plant embryo 42. As such, the adsorbent material 80 can completely or partially surround the plant embryo 42. The adsorbent material 80 need only fill, either completely or partially, one or two sides of the space between the plant embryo 42 and the walls of the cavity.

The adsorbent material 80 in the cavity 34 may be charcoal. Preferably, the charcoal is in the form of a powder and is activated by pretreatment with an acid such as HCl or phosphoric acid. Activated charcoal is commercially available. For example, powdered activated carbon NORIT® CNSP or DARCO® KB-G are available from Norit Americas Inc., Marshall, Tex. The adsorbent material 80 in the cavity 34 may be nutrient-treated charcoal. An exemplary method of preparing nutrient-treated charcoal for insertion into the cavity 34 is described in Example 2.

As used herein, a "plant embryo" refers to either a zygotic plant embryo or a somatic plant embryo. A zygotic plant embryo is an embryo found inside a botanic seed produced by sexual reproduction. Somatic embryos can be produced by culturing embryogenic tissue by standard methods under laboratory conditions in which the cells comprising the tissue are separated from one another and urged to develop into minute complete embryos.

As used herein, "a plant somatic embryo" refers to an embryo produced by culturing totipotent plant cells such as meristematic tissue under laboratory conditions in which the cells comprising the tissue are separated from one another and urged to develop into minute complete embryos. Alternatively, somatic embryos can be produced by inducing "cleavage polyembryogeny" of zygotic embryos. Methods for producing plant somatic embryos suitable for use in the methods of the invention are standard in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). For example, plant tissue may be cultured in an initiation media that includes hormones to initiate the formation of embryogenic cells, such as embryonic suspensor masses that are capable of developing into somatic embryos. The embryogenic cells may then be further cultured in a maintenance media that promotes establishment and multiplication of the embryogenic cells. Subsequently, the multiplied embryogenic cells may be cultured in a development media that promotes the development of somatic embryos, which may further be subjected to post-development treatments such as cold-treatments. The somatic embryos used in the methods of the invention have completed the development stage of the somatic embryogenesis process. They may also have been subjected to one or more post-development treatments.

Plant embryos suitable for use in the methods of the invention may be from a wide variety of plant species, such as dicotyledonous or monocotyledonous plants, gymnosperms, etc., and are not limited to any particular species. One type of plant embryo suitable for use in the methods of the invention is coniferales. Conifer embryos suitable for use in the methods of the invention may be from conifer species, including, but not limited to, Loblolly pine embryos and Douglas fir embryos. For use in manufactured seeds 20 according to the present invention, the plant embryo 42 is typically developed sufficiently to have a shoot end and a radicle end. In certain species of plants, the shoot end includes one or more cotyledons in some stage of development. In other types of plants, the cotyledon(s) are situated in locations other than the shoot end.

An exemplary method for assembling a plant embryo into a manufactured seed and germinating manufactured seeds is described in Example 3.

The methods of the invention are effective in preventing flooding of a manufactured seed, as shown in Example 4, without having an adverse effect on embryo development, as also shown in Example 4.

The following examples are provided for the purpose of illustrating, not limiting, the invention.

EXAMPLES

Example 1

This example is a representative method of preparation of a suitable nutritive media for use in the invention.

Nutritive Complete Media (KE64-50) is made by combining KE64 Basic Media (Table 1) with the components from Table 2, as described. KE64-50 is prepared from pre-made stocks. The required amount of each stock solution (that is not heat-labile) is added to water. Nonstock chemicals (such as charcoal and agar) are weighed out and added directly to the media. After all the nonheat-labile chemicals and compounds are added, the media is brought up to an appropriate volume and the pH is adjusted to 5.7. The media is then sterilized by autoclaving for 25 minutes.

TABLE 1

FORMULATION OF KE64 BASIC MEDIA

| Media Component | Final Concentration (mg/L) |
|---|---|
| $NH_4NO_3$ | 301.1 |
| $H_3BO_3$ | 10.0 |
| $(NH_4)_2MoO_4$ | 0.06 |
| $CaCl_2$—$2H_2O$ | 299.2 |
| $KH_2PO_4$ | 1800.0 |
| $MgSO_4$—$7H_2O$ | 1000.0 |
| $MnCl_2 \cdot 4H_2O$ | 6.0 |
| $ZnSO_4$—$7H_2O$ | 0.8 |
| $CuCl_2$—$2H_2O$ | 0.5 |
| Ferric Citrate | 60 |
| Pluronic F-68 | 10 g/L |
| Agar | 26-30 g/L |
| Nutrient-treated Charcoal | 60 g/L |

Filter-sterilized heat-labile components (Table 2) are added after the media has cooled to 40° C.

TABLE 2

| Media Component | Final Concentration mM | Final Concentration (mg/L) |
|---|---|---|
| Myo-inositol | 0.5549 | 100.0 |
| Thiamine-HCl | 0.0030 | 1.0 |
| Pyridoxine-HCl | 0.0012 | 0.25 |
| Nicotinic acid | 0.0081 | 1.0 |
| Riboflavin | 0.0021 | 0.125 |
| Ca-pantothenate |  | 0.50 |
| Biotin | 0.0003 | 0.0010 |
| Folic acid | 0.8077 | 0.1250 |
| L-asparagine | 1.8255 | 106.7 |
| L-glutamine | 0.3646 | 266.7 |
| L-lysine-2HCl | 0.7612 | 53.3 |
| DL-serine | 0.4631 | 80 |
| L-proline | 1.5310 | 53.3 |
| L-arginine-HCl | 0.4552 | 266.7 |
| Urea | 13.3200 | 800 |
| L-valine | 0.5983 | 53.3 |
| L-alanine | 0.2203 | 53.3 |
| L-leucine | 0.2448 | 80 |
| L-threonine | 0.3226 | 26.7 |
| L-phenylalanine | 0.1720 | 53.3 |
| L-histidine | 0.1308 | 26.7 |
| L-tryptophan | 0.2035 | 26.7 |
| L-isoleucine | 1.2930 | 26.7 |
| L-methionine | 0.7100 | 26.7 |
| L-glycine | 0.0003 | 53.3 |
| L-tyrosine | 0.2242 | 53.3 |

TABLE 2-continued

| Media Component | Final Concentration mM | Final Concentration (mg/L) |
|---|---|---|
| L-cysteine | 0.6098 | 26.7 |
| Sucrose |  | 50 g/L |
| Gibberillic Acid ($GA_{4/7}$) |  | 0.1 |
| Antimicrobials |  | 1.0 ml/L |

Example 2

This example is a representative method of preparing nutrient-treated charcoal suitable for use in the invention. KE64 Basic Media (Table 1) is prepared as described in Example 1, without Pluronic F-68 and without agar. Nutrient-treated charcoal is prepared as follows: 23.3 grams of 100-mesh charcoal is added to 1 liter of KE64 Basic Media. The components are autoclaved and allowed to cool to 40° C. The components of Table 2, as described in Example 1, are added sterilely to the KE64 Basic Media and the media is stirred to mix the components. The media is filtered through Whatman #1 filter paper in a Buchner funnel to collect the charcoal. A moisture balance is used to determine the moisture content of the charcoal cake and the dry weight of the charcoal is calculated. If the nutrient-loaded charcoal is to be added to the cavity of the manufactured seed, it is first dried until it becomes flowable matter.

Example 3

This example is a representative method of assembling plant embryos into manufactured seeds and germinating manufactured seeds. In an exemplary method for preparing a manufactured seed for use in the invention, the seed coat is prepared by sectioning polycaprolactone tubing to the appropriate length. Ceramic shoot restraints are made by injecting a porcelain slip into a preformed mold with a pin in the center to create the shoot accepting cavity. The slip is allowed to dry to a consistency that allows removal of the preformed restraint. The restraint is subsequently heated to a temperature that allows the porcelain to form a porous, but fused structure. The restraint can be acid washed to remove impurities, if desired. Lids are made by pre-stretching Parafilm™ (Pechiney Plastic Packaging, Chicago, Ill. 60631).

Zygotic embryos are prepared from botanic seeds. The seeds are surface-sterilized by methods similar to those previously described (Cyr et al., Seed Sci. Res. 1:91-97 (1991)). The seeds are cracked open and the zygotic embryos are dissected from the megagametophyte with scalpel and forceps in a laminar flow hood.

Somatic embryos are produced according to standard methods previously described (see, e.g., U.S. Pat. Nos. 4,957, 866; 5,034,326; 5,036,007; 5,041,382; 5,236,841; 5,294,549; 5,482,857; 5,563,061; and 5,821,126). For example, plant tissue may be cultured in an initiation media that includes hormones to initiate the formation of embryogenic cells, such as embryonic suspensor masses that are capable of developing into somatic embryos. The embryogenic cells may then be further cultured in a maintenance media that promotes establishment and multiplication of the embryogenic cells. Subsequently, the multiplied embryogenic cells may be cultured in a development media that promotes the development of somatic embryos, which may further be subjected to post-development treatments such as cold treatments. The somatic embryos used in the methods of the invention have completed the development stage of the somatic embryogenesis process. They may also have been subjected to one or more post-development treatments.

Manufactured seed are assembled by thermobonding the ceramic shoot restraint 22 to the seed coat 24. The seed coat 24 is then filled with nutritive media 26 and an embryo is inserted into the cavity 34 in the cotyledon restraint 22, cotyledon end first. Dry charcoal fill material 80 (either nutrient-treated or non-nutrient-treated) may be loaded into the cotyledon restraint after the embryo is inserted into the cavity 34. After the charcoal has been added, the seeds are then sealed with a secondary end seal by laying it over the open end of the seed and fusing the lids to the surface with heat. The primary end seals are dipped into blue wax mixture prior to attaching the secondary end seal. This promotes good bonding between the primary and secondary end seals. The seeds are then swabbed with anti-microbial agents.

A suitable amount of sterile sand is prepared by baking 2 liters of sand at a temperature of 375° F. for 24 hours. The sand is then added to pre-sterilized trays and 285 ml water is added. Furrows are then formed and the box is sealed. The box containing the sand is then autoclaved for 1 hour at 121° C. and 1 atmospheric pressure.

The manufactured seeds are sown in the sand and allowed to germinate. Typically, the manufactured seeds are cultured under continuous light at room temperature (23° C.) for four to five weeks.

Example 4

This example describes a comparison of the effect of various concentrations of agar in the nutritive media used in manufactured seed on flooding of the cavity of the manufactured seed, and on development of the embryos disposed therein.

Manufactured seeds were assembled as described in Example 3. Nutritive media was prepared as described in Example 1, with varying concentrations of agar, as described in each treatment below, and added to the manufactured seeds. Zygotic Loblolly pine embryos were inserted into the seeds (one embryo per seed) and nutrient-treated charcoal was added to the cavity. The seeds were then allowed to germinate as described in Example 3. The treatments are described below.

Treatment 1: KE64 Complete Media+18 g/L agar
Treatment 2: KE64 Complete Media+22 g/L agar
Treatment 3: KE64 Complete Media+26 g/L agar
Results Data was collected at 25 days past sowing.

Flooding. The presence of water in the seed cavity was observed visually. The percentage of seeds that were flooded in each treatment is shown in Table 3.

TABLE 3

Flooding Observations

| Treatment | Population (N) | Dry Cavity | Wet Cavity | Flooded Cavity |
|---|---|---|---|---|
| 1 (18 g/L agar) | 27 | 85% | 7% | 7% |
| 2 (22 g/L agar) | 28 | 79% | 7% | 11% |
| 3 (26 g/L agar) | 28 | 100% | 0% | 0% |

The data in Table 3 illustrates that 26 g/L concentration of agar in the nutritive media resulted in 100% of the cavities being dry, without noticeable signs of accumulated water. Seeds having nutritive media with lower concentrations of agar (18 g/L and 22 g/L) experienced some flooding.

Normalcy.

The normalcy of the germinants was also assessed and is shown in Table 4. The embryos were examined and classified as normal; would be normal if fully extracted from the cavity; not normal; fully extracted from the cavity, but not normal; and unchanged. The term "normal germinant" or "normalcy" denotes the presence of all expected parts of a plant at time of evaluation. The lengths of the radicle, hypocotyl, cotyledons, and epicotyl were measured to assess normalcy. The term "radicle" refers to the part of a plant embryo that develops into the primary root of the resulting plant. The term "cotyledon" refers generally to the first, first pair, or first whorl (depending on the plant type) of leaf-like structures on the plant embryo that function primarily to make food compounds in the seed available to the developing embryo, but in some cases act as food storage or photosynthetic structures. The term "hypocotyl" refers to the portion of a plant embryo or seedling located below the cotyledons but above the radicle. The term "epicotyl" refers to the portion of the seedling stem that is above the cotyledons. In the case of gymnosperms, normalcy is characterized by the radicle having a length greater than 3 mm and no visibly discernable malformations compared to the appearance of embryos germinated from natural seed. "Not normal" means tissue on at least one organ is swollen, and the root and cotyledons are dead. "Unchanged" means embryo has not changed from day one of the experiment.

TABLE 4

Normalcy

| Treatment | Normal $\alpha = 0.9674$ | Would be Normal if Fully Extracted $\alpha = 0.7900$ | Not Normal $\alpha = 0.2320$ | Unchanged $\alpha = 0.4021$ |
|---|---|---|---|---|
| 1 (18 g/L agar) | 63.1% | 20.0% | 4.2% | 7.0% |
| 2 (22 g/L agar) | 65.8% | 6.1% | 7.0% | 12.5% |
| 3 (26 g/L agar) | 60.3% | 11.6% | 9.7% | 0.0% |

The data in Table 4 illustrates that higher concentrations of agar in the nutritive media (26 g/L) did not have an adverse effect on normal development of the embryos as compared to lower concentrations of agar in the nutritive media (18 g/L and 22 g/L).

While illustrative embodiments have been illustrated and described, it will be appreciated that various changes can be made therein without departing from the spirit and scope of the invention.

The invention claimed is:

1. A manufactured seed comprising:
   (a) a seed coat;
   (b) a shoot restraint, wherein the shoot restraint comprises a cavity; and
   (c) a nutritive media comprising agar at a concentration from about 26 g/L to about 30 g/L, whereby the concentration of agar in the nutritive media lowers the water potential of the nutritive media, wherein the water potential of the nutritive media relative to the water potential of an embryo disposed in the cavity of the shoot restraint is such that an excessive amount of water does not flow out of the nutritive media and accumulate within the cavity, thereby preventing flooding of the cavity.

2. The manufactured seed of claim 1, wherein the concentration of agar in the nutritive media is from about 26 g/L to about 28 g/L.

3. The manufactured seed of claim 1, wherein the concentration of agar in the nutritive media is about 26 g/L.

4. The manufactured seed of claim 1, further comprising an adsorbent material within the cavity of the shoot restraint.

5. The manufactured seed of claim 4, wherein the adsorbent material is charcoal.

6. The manufactured seed of claim 1, wherein the adsorbent material is nutrient-treated charcoal.

7. The manufactured seed of claim 1, further comprising a plant embryo disposed in the cavity of the shoot restraint.

8. A nutritive media comprising agar at a concentration from about 26 g/L to about 30 g/L for use in a manufactured seed, wherein the manufactured seed comprises a seed coat, a shoot restraint, and a cavity within the shoot restraint, whereby the concentration of agar in the nutritive media lowers the water potential of the nutritive media, wherein the water potential of the nutritive media relative to the water potential of an embryo disposed in the cavity of the shoot restraint is such that an excessive amount of water does not flow out of the nutritive media and accumulate within the cavity, thereby preventing flooding of the cavity.

9. The nutritive media of claim 8, wherein the concentration of agar in the nutritive media is from about 26 g/L to about 28 g/L.

10. The nutritive media of claim 8, wherein the concentration of agar in the nutritive media is about 26 g/L.

\* \* \* \* \*